(12) United States Patent
Jadhav et al.

(10) Patent No.: US 8,183,388 B2
(45) Date of Patent: May 22, 2012

(54) ANDROGEN RECEPTOR MODULATOR AND USES THEREOF

(75) Inventors: Prabhakar Kondaji Jadhav, Zionsville, IN (US); Venkatesh Krishnan, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 21 days.

(21) Appl. No.: 12/943,163

(22) Filed: Nov. 10, 2010

(65) Prior Publication Data

US 2011/0118326 A1    May 19, 2011

Related U.S. Application Data

(60) Provisional application No. 61/261,022, filed on Nov. 13, 2009.

(51) Int. Cl.
*C07D 209/82* (2006.01)
*A61K 31/403* (2006.01)

(52) U.S. Cl. ..................... 548/449; 514/411

(58) Field of Classification Search .............. 548/449; 514/411

See application file for complete search history.

(56) References Cited

FOREIGN PATENT DOCUMENTS

WO 2007002181 1/2007
WO 2008063867 5/2008

*Primary Examiner* — Robert Havlin
(74) *Attorney, Agent, or Firm* — Elizabeth Dingess-Hammond

(57) ABSTRACT

The present invention relates to the compound of the formula:

Formula (I)

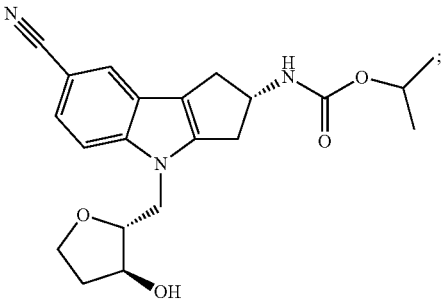

to pharmaceutical compositions comprising the compound of Formula (I); and to methods for treating or preventing hypogonadism, osteoporosis, osteopenia, sarcopenia, cachexia, muscle atrophy, sexual dysfunction or erectile dysfunction, comprising administering to a patient in need thereof an effective amount of the compound of Formula (I).

8 Claims, No Drawings

ANDROGEN RECEPTOR MODULATOR AND USES THEREOF

The present invention is in the field of androgen receptor modulators for therapeutic use.

Endogenous steroidal androgens (e.g. testosterone and 5α-dihydrotestosterone (DHT)) are the major circulating sex hormone and play a role in the regulation of various physiological processes. Anabolic (e.g. tissue building) effects of androgens include increasing muscle mass and strength and increasing bone mass and density, whereas androgenic (e.g. masculinizing) effects include development of the internal reproductive tissues (e.g. prostate and seminal vesicles), the external genitalia, male hair growth patterns, and libido. Clinically, androgen replacement therapy has been used in the treatment of various conditions and disorders including male hypogonadism, osteoporosis, muscle wasting diseases, and sexual or erectile dysfunction.

However, steroidal androgen therapy has limitations. For example, preparations of steroidal androgens have been found to suffer from rapid degradation in the liver leading to poor oral bioavailability and short duration of activity following parenteral administration, variations in plasma levels, hepatotoxicity, or cross reactivity with other steroid hormone receptors (e.g. the glucocorticoid receptor (GR), the mineralocorticoid receptor (MR), or the progesterone receptor (PR)). Furthermore, unwanted side effects are associated with steroidal androgen therapy including growth stimulation of the prostate and seminal vesicles, stimulation of prostate tumors and elevations in prostate specific antigen (PSA), and the risk of hirsutism or virilization in females.

Thus, there remains a need in the art for alternatives to steroidal androgen therapy. In particular, there remains a need for nonsteroidal androgen receptor (AR) ligands which possess androgen agonist activity. More particularly, there remains a need for nonsteroidal AR agonists which bind to AR with greater affinity relative to the other steroid hormone receptors. Even more particularly, there remains a need for tissue-selective androgen receptor modulators (SARMs) which display androgen agonist activity in anabolic tissues such as muscle or bone, but only partial agonist, partial antagonist or antagonist activity in androgenic tissues such as the prostate or seminal vesicle.

Published international patent application WO 2008/063867 and Co-pending international patent application PCT/US2009/043875 each disclose a series of cyclopenta[b]indole compounds useful as androgen receptor modulators. Still, there remains a need for further cyclopenta[b]indole compounds with improved potency and/or pharmacokinetic characteristics such as exposure or bioavailability.

The present invention is directed to a cyclopenta[b]indole compound, as defined by Formula (I) below, which has particular profiles of activity in in vitro and in vivo testing which suggest it is useful in the treatment of disorders responsive to steroidal androgen therapy. Thus, the present invention provides a compound of Formula (I):

Formula (I)

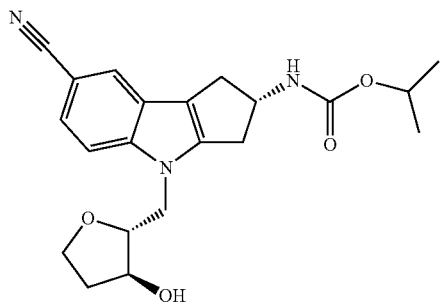

[(S)-7-Cyano-4-((2R,3S)-3-hydroxytetrahydrofuran-2-ylmethyl)-1,2,3,4-tetrahydrocyclopenta[b]indol-2-yl]-carbamic acid isopropyl ester In another embodiment, the present invention provides a method of treating or preventing hypogonadism, osteoporosis, osteopenia, sarcopenia, cachexia, muscle atrophy, sexual dysfunction or erectile dysfunction comprising administering to a patient in need thereof an effective amount of the compound of Formula (I). In a particular aspect, the present invention provides a method of treating or preventing osteoporosis, osteopenia, muscle atrophy or erectile dysfunction comprising administering to a patient in need thereof an effective amount of the compound of Formula (I). In a further particular aspect, the present invention provides a method of treating or preventing muscle atrophy associated with disuse, trauma, immobilization, spinal cord injury or stroke comprising administering to a patient in need thereof an effective amount of the compound of Formula (I). Even more particularly, the present invention provides a method of treating or preventing muscle atrophy associated with hip or knee replacement, hip fracture, spinal cord injury or stroke comprising administering to a patient in need thereof an effective amount of the compound of Formula (I).

Further, the present invention provides the compound of Formula (I) for use in the treatment or prevention of hypogonadism, osteoporosis, osteopenia, sarcopenia, cachexia, muscle atrophy, sexual dysfunction or erectile dysfunction. More particularly, the invention provides the compound of Formula (I) for use in the treatment or prevention of osteoporosis, osteopenia, muscle atrophy or erectile dysfunction. In a further particular aspect, the present invention provides the compound of Formula (I) for use in the treatment or prevention of muscle atrophy associated with disuse, trauma, immobilization, spinal cord injury or stroke. Even more particularly, the present invention provides the compound of Formula (I) for use in the treatment or prevention of muscle atrophy associated with hip or knee replacement, hip fracture, spinal cord injury or stroke. In addition, the present invention provides the compound of Formula (I) for use in therapy.

In another embodiment, the present invention provides the use of the compound of Formula (I) for the manufacture of a medicament for the treatment or prevention of hypogonadism, osteoporosis, osteopenia, sarcopenia, cachexia, muscle atrophy, sexual dysfunction or erectile dysfunction. More particularly, the present invention provides the use of the compound of Formula (I) for the manufacture of a medicament for the treatment or prevention of osteoporosis, osteopenia, muscle atrophy or erectile dysfunction. In a further particular aspect, the present invention provides the use of the compound of Formula (I) for the manufacture of a medicament for the treatment or prevention of muscle atrophy associated with disuse, trauma, immobilization, spinal cord injury or stroke. Even more particularly, the present invention provides the use of the compound of Formula (I) for the manufacture of a medicament for the treatment or prevention of muscle atrophy associated with hip or knee replacement, hip fracture, spinal cord injury or stroke.

The present invention also provides a pharmaceutical composition comprising the compound of Formula (I) in combination with one or more pharmaceutically acceptable carriers, diluents, or excipients. In particular, the present invention provides a pharmaceutical composition for the treatment or prevention of hypogonadism, osteoporosis, osteopenia, sarcopenia, cachexia, muscle atrophy, sexual dysfunction or erectile dysfunction comprising the compound of Formula (I) in combination with one or more pharmaceutically acceptable carriers, diluents or excipients. More particularly, the present invention provides a pharmaceutical composition for the treatment or prevention of osteoporosis, osteopenia, muscle atrophy or erectile dysfunction comprising the compound of Formula (I) in combination with one or more pharmaceutically acceptable carriers, diluents or excipients. More particularly, the present invention provides a pharmaceutical composition for the treatment or prevention of muscle atrophy associated with disuse, trauma, immobilization, spinal cord injury or stroke comprising the compound of Formula (I) in combination with one or more pharmaceutically acceptable carriers, diluents or excipients. Even more particular, the present invention provides a pharmaceutical composition for the treatment or prevention of muscle atrophy associated with hip or knee replacement, hip fracture, spinal cord injury or stroke comprising the compound of Formula (I) in combination with one or more pharmaceutically acceptable carriers, diluents or excipients. In yet a further embodiment, the pharmaceutical composition of the present invention further comprises one or more additional therapeutic agents.

The present invention also encompasses intermediates and processes useful for the synthesis of the compound of Formula (I).

The compound of Formula (I), and the intermediates predicate thereto, have chiral centers and the particular stereoisomeric configurations as disclosed herein. The terms "R" and "S" are used herein as commonly used in organic chemistry to denote specific configurations of a chiral center. The terms "(±)" or "RS" refer to a configuration of a chiral center comprising a racemate. A partial list of priorities and a discussion of stereochemistry is contained in "Nomenclature of Organic Compounds: Principles and Practice", (J. H. Fletcher, et al., eds., 1974). Specific stereoisomers and enantiomers can be prepared by one of ordinary skill in the art utilizing well known techniques and processes. For example, specific stereoisomers and enantiomers can be prepared by stereospecific syntheses using enantiomerically and geometrically pure, or enantiomerically or geometrically enriched starting materials. In addition, specific stereoisomers and enantiomers can be resolved and recovered by techniques such as chromatography on chiral stationary phases, enzymatic resolution, fractional recrystallization of addition salts, as well as those techniques provided in the Schemes, Preparations and Examples herein. In addition, the compound of the present invention may exist as a solvate. Thus, the compound of Formula (I) includes within its meaning any solvate of the compound.

The designation "◂▬" refers to a bond that protrudes forward out of the plane of the page.

The designation "⋯⋯◁" refers to a bond that protrudes backward out of the plane of the page.

The designation "∿∿∿" refers to a bond that exists as a mixture of bonds that protrude both forward and backward out of the plane of the page.

Androgens and non-steroidal androgen receptor agonists have been used clinically or pre-clinically in a variety of therapeutic applications, thus, methods for the treatment or prevention of symptoms, conditions or disorders responsive to androgen receptor agonism are an important additional aspect of the present invention. The compound of the present invention may be administered, or used in a medicament, either alone or in combination with other conventional therapeutic agents used to treat a particular symptom, condition, or disorder. Where the compounds of the present invention is used as part of a combination, the compound of Formula (I) may be administered either separately, or as part of a formulation comprising the therapeutic agent with which it is to be combined.

A particular method in which the compound of the present invention is believed useful is in the treatment or prevention of muscle wasting conditions or muscle atrophy. Muscle wasting may occur as a natural result of aging (e.g. sarcopenia). Alternatively, muscle atrophy may result as a secondary consequence of disuse or inactivity (e.g. following hip or knee replacement or hip fracture), trauma, immobilization (e.g. casting or splinting of limbs), as well as spinal cord injury or stroke. (See, Hafer-Macko et al., *J. Rehab. Res. Develop.*; 45(2): 261-272 (2008)) Thus, as used herein, the term "muscle atrophy associated with disuse, trauma, immobilization, spinal cord injury or stroke" refers to muscle atrophy that occurs as a secondary consequence to the incidence of disuse or inactivity (e.g. following hip or knee replacement or hip fracture), trauma, immobilization (e.g. casting or splinting of limbs), spinal cord injury or stroke. Furthermore, in the context of spinal cord injury or stroke, the compound of the present invention may be used as an adjunct to standard rehabilitation therapy (e.g. physical or occupational therapy, exercise, assisted walking and/or strength training).

Another particular method in which the compound of the present invention is believed useful is in the treatment or prevention of erectile dysfunction. Conventional agents for the treatment of erectile dysfunction include the phosphodiesterase type 5 (PDE5) inhibitors tadalafil (Cialis® or Cialis® for daily use), sildenafil citrate (Viagra®) and vardenafil hydrochloride (Levitra®). Thus, the present invention also provides a method of treating or preventing erectile dysfunction comprising administering to a patient in need thereof an effective amount of the compound of Formula (I) in combination with an agent selected from the group consisting of tadalafil, sildenafil citrate, and vardenafil hydrochloride. More particularly, the present invention provides a method of treating or preventing erectile dysfunction comprising administering to a patient in need thereof an effective amount of the compound of Formula (I) in combination with an agent selected from the group consisting of Cialis®, Cialis® for daily use, Viagra® and Levitra®. Furthermore, the present invention also provides the compound of Formula (I) for use in combination with an agent selected from the group consisting of tadalafil, sildenafil citrate, and vardenafil hydrochloride, in the treatment of erectile dysfunction. More particularly, the present invention provides the compound of Formula (I) for use in combination with an agent selected from the group consisting of Cialis®, Cialis® for daily use, Viagra® and Levitra®, in the treatment of erectile dysfunction.

The compound of the present invention may be formulated as part of a pharmaceutical composition. As such, a pharmaceutical composition comprising the compound of Formula (I) in combination with one or more pharmaceutically acceptable carriers, diluents or excipients is an important aspect of the present invention. As a further aspect, the present invention also provides a pharmaceutical composition comprising the compound of Formula (I) wherein such composition comprises one or more additional therapeutic agents. In particular, the present invention provides a pharmaceutical composition comprising: (a) the compound of Formula (I); (b) a therapeutic agent selected from the group consisting of tadalafil, sildenafil citrate, and vardenafil hydrochloride; and (c) a pharmaceutically acceptable carrier, diluent or excipient. More particularly, the present invention provides a pharmaceutical composition comprising: (a) the compound of Formula (I); (b) a therapeutic agent selected from the group consisting of Cialis®, Cialis® for daily use, Viagra® and Levitra®; and (c) a pharmaceutically acceptable carrier, diluent or excipient. Examples of pharmaceutical compositions and methods for their preparation are well known in the art.

As used herein the term "patient" refers to a human or nonhuman mammal, and preferably refers to a human. The term "treating" (or "treat" or "treatment") as used herein refers to prohibiting, restraining, slowing, stopping, or reversing the progression or severity of an existing symptom, condition or disorder. The term "preventing" (or "prevent" or "prevention") as used herein refers to prohibiting, restraining, or inhibiting the incidence or occurrence of a symptom, condition or disorder. Symptoms, conditions, or disorders may present as "acute" or "chronic" events. In an acute event compound is administered at the onset of symptom, condition, or disorder and discontinued when the event disappears, whereas a chronic symptom, condition, or disorder is treated throughout the course of the event. The present invention contemplates both acute and chronic treatment.

As used herein the term "effective amount" refers to the amount or dose of the compound of Formula (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications. The compound of Formula (I), or a composition comprising the compound of Formula (I) may be administered by any route which makes the compound bioavailable, including oral and parenteral routes (e.g. subcutaneous, intravenous, intraperitoneal, intramuscular, or transdermal).

Determination of Biological Activity:

As evidenced by in vitro and in vivo testing, the compound of Formula (I) possesses a profile of activity which suggests it has utility in the treatment of symptoms, conditions or disorders responsive to steroidal androgen therapy. In particular, compound of Formula (I) is a potent AR agonist that selectively binds to AR relative to each of MR, GR, and PR.

As used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "$K_b$" refers to the equilibrium dissociation constant for an antagonist-receptor complex; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; "ED50" refers to the dose of an administered therapeutic agent which produces 50% of the maximal response for that agent; "SD" refers to standard deviation; "p.o." stands for per os and refers to oral administration; "s.c." refers to subcutaneous administration; and "HEC" refers to hydroxyethyl cellulose.

Steroid Hormone Nuclear Receptor Binding Assay:

Cell lysates from human embryonic kidney HEK293 cells overexpressing human MR (mineralocorticoid receptor), GR (glucocorticoid receptor), AR (androgen receptor), or PR (progesterone receptor) are used for receptor-ligand competition binding assays to determine $K_i$ values. Typical procedures are provided below Briefly, steroid receptor competition binding assays are run in a buffer containing 20 mM HEPES buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 µg/mL aprotinin and 20 µg/mL leupeptin (assay buffer). Typically, steroid receptor binding assays include radio-labeled ligands, such as 0.25 nM [$^3$H]-aldosterone for MR binding, 0.3 nM [$^3$H]-dexamethasone for GR binding, 0.36 nM [$^3$H]-methyltrienolone for AR binding, and 0.29 nM [$^3$H]-methyltrienolone for PR binding, and either 20 µg 293-MR lysate, 20 µg 293-GR lysate, 22 µg 293-AR lysate, or 40 µg 293-PR lysate per well. Assays are typically run in 96-well format. Competing test compounds are added at various concentrations ranging from about 0.01 nM to 10 µM. Non-specific binding is determined in the presence of 500 nM aldosterone for MR binding, 500 nM dexamethasone for GR binding, or 500 nM methyltrienolone for AR and PR binding. The binding reactions (140 µL) are incubated overnight at 4° C., then 70 µL of cold charcoal-dextran buffer (containing per 50 mL of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 µL of the binding reaction mixture is then transferred to another 96-well plate and 175 µL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 µM. The Kd for [$^3$H]-aldosterone for MR binding, [$^3$H]-dexamethasone for GR binding, [$^3$H]-methyltrienolone for AR binding, or [$^3$H]-methyltrienolone for PR binding, is determined by saturation binding. The IC50 values for compounds are converted to Ki using the Cheng-Prushoff equation.

Following a protocol essentially as described above, the compound of Formula (I) displayed a $K_i$ in the AR binding assay of about 10 nM. Furthermore, the compound displayed a $K_i$ in the MR, GR, and PR binding assays of greater than about 4000 nM, greater than about 2000 nM, and greater than about 4000 nM, respectively. Thus, the compound of Formula (I) is a high-affinity, selective ligand for the androgen receptor.

Functional Assays of Steroid Nuclear Hormone Receptor Modulation:

Androgens exerts their physiological effects through interaction with the androgen receptor. Following cytoplasmic binding of an androgen to AR, the ligand receptor complex translocates to the cell nucleus where it binds to hormone response elements on DNA to initiate expression of target genes. The effects of androgens may be characterized as anabolic or androgenic in nature. Anabolic (i.e. tissue building) effects of androgens include increasing muscle mass and strength and bone mass, whereas androgenic (i.e. masculinizing) effects include the development of male secondary sexual characteristics such as the internal reproductive tissues (i.e. prostate and seminal vesicle), the external genitalia (penis and scrotum), libido, and hair growth patterns.

To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art. The following provides typical procedures for nuclear hormone receptor functional assays.

A. Nuclear Hormone Receptor Panel Screen

Human embryonic kidney HEK293 cells are transfected with steroid hormone receptor and reporter gene plasmids using a suitable transfection reagent such as Fugene™. Briefly, the reporter plasmid containing two copies of probasin ARE and TK (thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 µM. In the antagonist mode for the assays, low concentrations of agonist for each respective receptor are added to the media (0.08 nM aldosterone for MR, 0.25 nM dexamethasone for GR, 0.66 nM of methyltrienolone for AR, and 0.08 nM of promegestone for PR). After 24 hours incubation with test compounds, cells are lysed and luciferase activity is determined using standard techniques.

Data are fitted to a four parameter-fit logistic curve to determine EC50 values. The percentage efficacy (compounds with saturated maximum responses) or the percent maximum stimulation (compounds with maximum responses that do not saturate) are determined relative to maximum stimulation obtained with the following reference agonists: 30 nM aldosterone for MR assay, 100 nM methyltrienolone for AR assay, 30 nM promegestone for PR assay, and with 100 nM dexamethasone for GR assay. IC50 values are determined similarly using antagonist mode assay data. In the antagonist mode, percent inhibitions are determined by comparing test compound activity in the presence of low concentration of agonist (0.08 nM aldosterone for MR, 0.25 nM dexamethasone for GR, 0.66 nM of methyltrienolone for AR, and 0.08 nM of promegestone for PR) to the response produced by the same low concentration of agonist in the absence of test compound.

B. C2C12 AR/ARE Reporter Assay:

As an indicator of agonist activity in muscle tissue, the C2C12 AR/ARE reporter assay is performed. Briefly, mouse myoblast C2C12 cells are co-transfected using Fugene™ reagent. A reporter plasmid containing a GRE/ARE (glucocorticoid response element/androgen response element) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% charcoal stripped Fetal Bovine Serum (FBS). After a 5 hour incubation, transfected cells are trypsinized, plated in 96 well dishes in DMEM media containing 4% charcoal-stripped FBS, incubated for 2 h and then exposed to various concentrations of test compounds ranging from about 0.01 nM to 10 µM. After 24 h of incubations with compounds, cells are lysed and luciferase activity is determined by standard techniques. Data is fit to a 4 parameter-fit logistics to determine EC50 values. The % efficacy is determined versus maximum stimulation obtained with 10 nM methyltrienolone.

Functional assays of steroid hormone nuclear hormone receptor modulation similar to those described above can be readily designed by the ordinarily skilled artisan. Following a protocol essentially as described above, the compound of Formula (I) displayed an EC50 in the C2C12 AR/ARE reporter assay of about 0.2 nM (geometric mean of n=7; SD of about 0.08), thus demonstrating that the compound of the present invention is an agonist of human AR.

In Vivo Model of Efficacy and Selectivity:

Eight week old male Sprague Dawley rats are castrated (gonadectomized or "GDX") according to approved procedures and allowed to waste for eight weeks. Age-matched sham-operated mice are also prepared. Animals are housed in a temperature-controlled room (24° C.) with a reversed 12 hour light/dark cycle and water and food are available ad libitum.

Animals are randomized based on body weight prior to ascribing a test slot. Test compound in vehicle, or vehicle alone, is administered daily by subcutaneous injection to the castrated 16 week old rats (body weight about 380-400 g) using a conventional vehicle such as 5% DMSO/95% soybean oil. Sham operated rats treated with vehicle alone are used as a treatment positive controls, whereas the castrated rats treated only with vehicle are used as treatment negative control. A separate cohort of castrated animals are treated with testosterone as a comparator.

Test animals are dosed daily over a two or eight week timeframe with, for example, 0.1, 0.3, or 1.0 mg/kg per day of the compound of the present invention, or weekly with 10 mg/kg per week of testosterone (sesame oil vehicle) After the treatment period the animals are sacrificed and the wet weight of the levator ani (LA) muscle, the prostate and the bulbocavernous muscle from each animal is determined (after weighing, the bulbocavernous muscle may be flash frozen in liquid nitrogen for later use in measuring neuronal nitric oxide synthase mRNA, as described below). The wet weights are then normalized by dividing each individual wet weight by the body weight of the corresponding animal at the end of the study. The normalized values from the treatment animals are then compared to the normalized values from the castrated, vehicle-only control group or the sham group. As an indicator of tissue selective activity, the wet weight of the prostate from test animals may be similarly compared to the wet weight of the prostate from the control groups or the testosterone-treated comparator group.

Following a protocol essentially as described above using a two week treatment period, studies with the compound of Formula (I) produced the following results: Sham (vehicle only) showed a mean (n=8) normalized LA wet weight value of about 0.72, a mean normalized prostate wet weight value of about 1.5, and a mean normalized bulbocavernous wet weight value of about 2.15; the castrated/vehicle only animals showed a mean (n=6) normalized LA wet weight value of about 0.18, a mean normalized prostate wet weight value of about 0.04, and a mean normalized bulbocavernous wet weight value of about 0.34; the 0.1 mg/kg per day study group showed a mean (n=6) normalized LA wet weight value of about 0.44, a mean normalized prostate wet weight value of about 0.04, and a mean normalized bulbocavernous wet weight value of about 0.77; the 0.3 mg/kg per day study group showed a mean (n=6) normalized LA wet weight value of about 0.57, a mean normalized prostate wet weight value of about 0.14, and a mean normalized bulbocavernous wet weight value of about 1.29; and the 1.0 mg/kg per day study group showed a mean (n=6) normalized LA wet weight value of about 0.68, a mean normalized prostate wet weight value of about 0.52, and a mean normalized bulbocavernous wet weight value of about 1.41.

Thus, treatment with the compound of Formula (I) produced a dose dependent increase in levator ani and bulbocavernous muscle weights in comparison to the castrated control group, demonstrating that the compound of the present invention is a potent androgen agonist in vivo. Furthermore, the compound of Formula (I) elicited efficacy in muscle while concomitantly producing a decreased effect on prostate weight when compared to Sham control and testosterone treated animals, thus demonstrating that the compound of the present invention has tissue selectivity.

In Vitro Assay of Erectile Activity

The nitric oxide synthase/cyclic guanosine monophosphate (NOS/cGMP) pathway is critical for erectile activity. NOS expression leads to nitric oxide (NO) generation which, in turn, promotes cGMP generation through activation of guanylyl cyclase. cGMP promotes protein kinase G (PKG) activity which mediates relaxation of corporal smooth muscle to facilitate penile erection. Evidence supports a role for androgens in regulating the expression and activity of NOS isoforms in the corpus cavernorsum in experimental animal models. Traish et al., *European Urology*, 52; 54-70 (2007). Thus, androgen receptor modulators, which are capable of increasing the expression of NOS isoforms, are believed to have a role in regulating penile erectile activity.

To determine the ability of compounds of the present invention to up-regulate the expression of NOS isoforms, the following in vitro methods may be employed.

RNA is isolated from frozen bulbous or corpus cavernosum tissues that are obtained at necropsy from castrated Sprague Dawley rats that are prepared and dosed essentially as described above for the Model of Efficacy and Selectivity. cDNA is synthesized from 2 μg of RNA using a high capacity cDNA kit according to the manufacturer's instructions.

Real-time quantitative PCR is then performed according to the fluorescent TaqMan® methodology (Applied Biosystems). Assays-on-Demand™ (Applied Biosystems) probes are used for the rat endothelial nitric oxide synthase transcript (eNOS) while probes are designed for the rat penile specific isoform of neuronal nitric oxide synthase (pnNOS) using probe designer software (Applied Biosystems). The probes are designed to span a 102 bp region of the rat neuronal nitric oxide synthase gene (pnNOS) that is specific to pnNOS (positions 2865-2967). Assays-on-Demand™ probe sets for the PPIB transcript are used as an internal control. PCR is performed on an ABI Prism 7700 Sequence Detection System at the following thermocycler conditions: 2 min. at 50° C., 10 min. at 95° C., and 40 cycles at 95° C. for 30 s, and 60° C. for 1 min. All reactions are carried out in triplicate.

Reductions in muscle mass or strength may occur as a result of disuse, trauma, or immobilization. In order to further determine the ability of compounds of the present invention to treat or prevent loss of muscle mass or strength associated with disuse, trauma, or immobilization the following animal models may be employed.

In Vivo Model of Muscle Loss Induced by Trauma and Immobilization

Male 12 week old ICR mice are anesthetized with isofluorane (1-5%) and the right gastrocnemius muscle of a hind limb is bilaterally injected with 100 μL of a 10 μM cardiotoxin (naja naja atra; Sigma Aldrich) to induce focal muscle injury. Animals are allowed to recover and within 24 h the hind limb is immobilized in the plantar flexion mode by placing a cast on the limb. Following seven days of immobilization, and upon removal of the hind limb cast, the mice are treated with a daily administration of the compound of the present invention for various time periods. Control animals, with and without casts, are similarly treated with vehicle for various time periods. At the end of the treatment protocol, the mice are sacrificed, the wet weights of the casted gastrocnemius are determined and the individual treatment groups are compared to the vehicle controls. See generally *Am. J. Endocrinol. Metab.* 289: 969-980 (2005).

In Vivo Model of Muscle Loss Induced by Trauma

Male ICR mice are castrated at 8 weeks of age and allowed to waste for an additional 8 weeks. The mice are individually caged and maintained on a 12 hr light/dark cycle at 22° C. with ad lib access to food and water. Mice are anesthetized with isofluorane (1-5%) and the right gastrocnemius muscle is bilaterally injected with 100 μL of a 10 μM cardiotoxin (naja naja atra; Sigma Aldrich) to induce muscle injury. Animals recover from anesthesia and resume normal activity within 5 minutes. On day 5 post injection animals are treated with various doses of a compound of the present invention. After day 14 post injection, the treated mice are euthanized, weighed, and the gastrocnemius muscle tissue is harvested from both uninjected (contra-lateral control) and cardiotoxin injected legs. The muscle weights are matched to the uninjected and untreated control to establish percentage recovery from trauma.

To demonstrate that the compound of the present invention has the capacity to treat disorders associated with bone loss, such as osteoporosis or osteopenia, other animal models well known to those in the art may be employed. Examples of such models are provided in Y. L. Ma et al., *Japanese Journal of Bone and Mineral Metabolism* 23 (Suppl.): 62-68 (2005); Y. L. Ma et al., *Endocrinology* 144: 2008-2015 (2003); and K. Hanada et al., *Biol. Pharm. Bull.* 26(11): 1563-1569 (2003). Particular mention is made of the Female Rat Model of Estrogen Deficiency Osteopenia induced by Ovariectomy, and the Male Rat Model of Androgen Deficiency Osteopenia induced by Orchidectomy.

Model of Estrogen Deficiency Osteopenia Induced by Ovariectomy:

Six-month-old, virgin Sprague Dawley female rats weighing about 220 g are housed with ad libitum access to food and water. Bilateral ovariectomies (Ovx) are performed on the animals (except for sham-operated controls) and then randomized into treatment groups of 7-8 rats per group. Each assay typically contains at least 2 sets of controls, including sham-ovariectomy (Sham) and ovariectomized controls (Ovx) treated with vehicle. Ovx rats are permitted to lose bone for 1 month to establish osteopenia before treatment with test compound. Test compounds are administered orally via gavage to Ovx animals for 8 weeks. As a positive control, recombinant human PTH (1-38) (about 10 μg/kg/d, subcutaneously) may be given to a subset of Ovx animals. Following completion of the testing protocol, Quantitative computed tomographic (QCT) is used to analyze the volumetric bone mineral density (BMD, mg/cc) of lumbar vertebra L-5 and the femur. Biomechanical analyses of three point bending on the femoral midshaft and load to failure on the proximal femur are performed using a material mechanical testing machine and analyzed using TestWorks 4® software.

Model of Androgen Deficiency Osteopenia Induced by Orchidectomy:

Six-month-old, Sprague Dawley male rats weighing about 485 g are housed with ad libitum access to food and water. Bilateral orchidectomy (Orx) are performed on the animals (except for sham-operated controls) and then randomized into the treatment groups of 7-8 rats per group. Each assay typically contains at least 2 sets of controls, including sham-orchidectomized (Sham) and orchidectomized controls (Orx) treated with vehicle. Orx rats are permitted to lose bone for 2 months to establish osteopenia before treatment with test compound is initiated. Test compounds are administered orally via gavage to Ovx animals for 8 weeks. As a positive control, recombinant human PTH (1-38) (about 10 ug/kg/d, subcutaneously) may be given to a subset of Orx animals. Following completion of the testing protocol, the BMD of the vertebra and femur, as well as the biomechanical analyses of the femur may be performed as described above for the ovariectomized female rat model.

(See generally, Ma et al., *JBMR* 17:2256-2264 (2002), and Turner et al., *Bone* [Review] 14:595-608 (1993)).

Determination of Plasma Exposure

Groups of male Sprague Dawley rats (6 animals/group) are dosed either orally (dosing volume of 1.25 ml/kg; vehicle of 5% DMSO/95% HEC) or subcutaneously (dosing volume of 2.5 ml/kg; vehicle of 5% DMSO/95% soybean oil) with 10 mg/kg p.o, 1 mg/kg s.c., 3 mg/kg s.c., or 10 mg/kg s.c. of the compound of Formula (I), once per day for two weeks. Starting on the second to last day of dosing, plasma samples are collected at 0.5, 2, 4, or 24 hours post-dosing (two animals are sampled at each time-point, with the same animals being used for the 0.5 and 24 hour time-point samples). The plasma concentration of the compound of Formula (I) is determined for each collected sample using LC/MS/MS (Sciex API-4000 LC/MS/MS system). The resulting concentrations are used to construct an area under the plasma concentration time curve (AUC) for each administered dose as an index of exposure. Following a protocol essentially as described above, the administered doses of the compound of Formula (I) produced the following AUC values: 10 mg/kg p.o: about 295,511 ng·hr./ml.; 1 mg/kg s.c.: about 38,963 ng·hr./ml.; 3 mg/kg s.c.: about 137,056 ng·hr./ml.; and 10 mg/kg s.c.: about 218,537 ng·hr./ml. Thus, the compound of Formula (I), when administered orally or subcutaneously, displays significant plasma exposure.

The following Schemes, Preparations and Example further illustrate the invention. The reagents and starting materials are readily available to, or may be readily synthesized by, one of ordinary skill in the art. It should be understood that the Schemes, Preparations and Example are set forth by way of illustration and not limitation, and that various modifications may be made by one of ordinary skill in the art. The R or S configuration of the Preparations and Example may be determined by standard techniques such as X-ray analysis and correlation with chiral-HPLC retention time. Unless otherwise indicated, the names of the Preparations and Example are generally provided by Autonom 2000 for ISIS Draw add-in. As used herein, the following terms have the meanings indicated: "MeOH" refers to methanol; "EtOH" refers to ethanol; "i-PrOH" or "IPA" refers to isopropanol; "EtOAc" refers to ethyl acetate; "DMAC" refers to dimethyl acetamide; "THF" refers to tetrahydrofuran; "t-boc" or "boc" refers to tert-butoxycarbonyl.

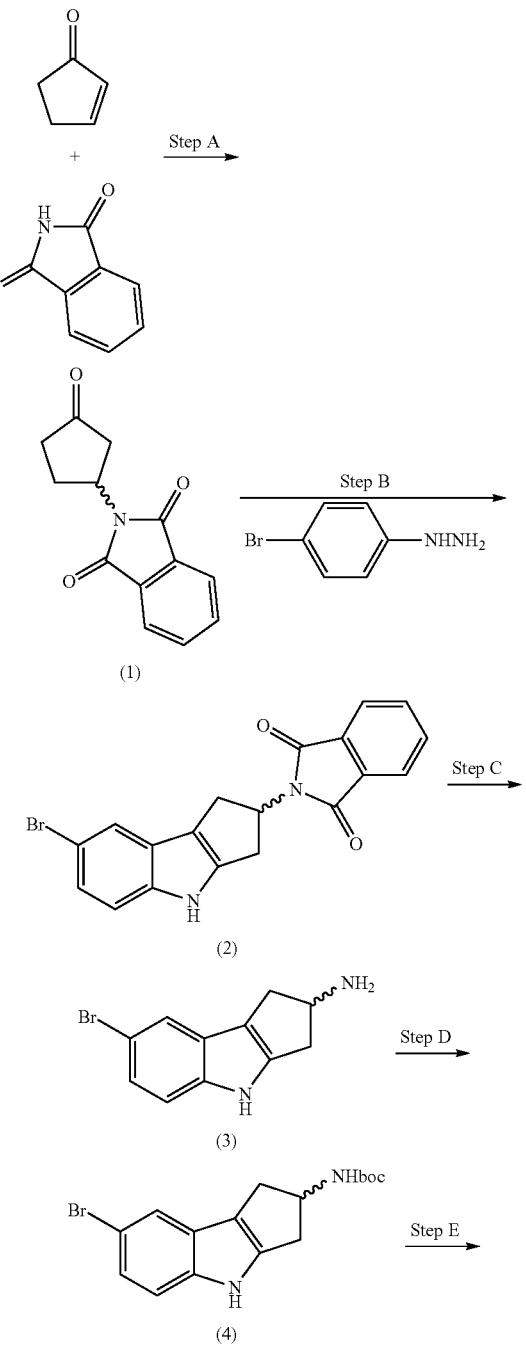

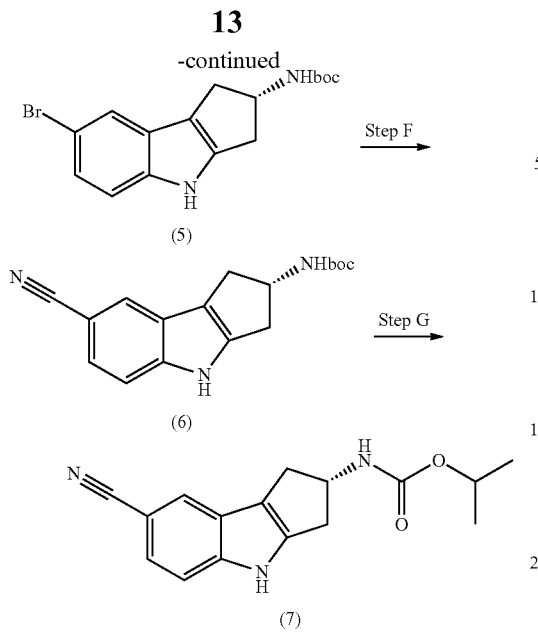

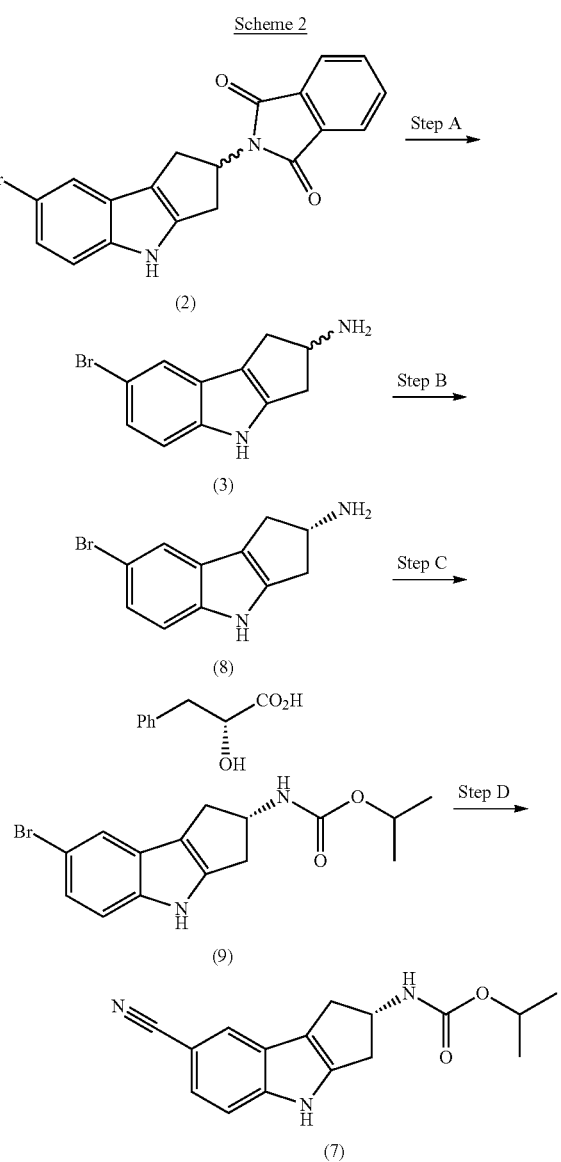

Formation of an intermediate of formula (7) can be carried out in accordance with reactions as depicted in Scheme 1.

In Scheme 1, Step A, cyclopentenone is reacted with phthalimide in a Michael addition to give (R,S)-2-(3-oxo-cyclopentyl)-isoindole-1,3-dione (1). The reaction is performed in methanol/2 N $Na_2CO_3$ in a ratio of about 10/1 by volume, preferably at ambient temperature using conditions similar to those described by O. Nowitzki, et. al. in *Tetrahedron* 1996, 52, 11799-11810. The product is isolated by addition of water and (1) obtained as a white solid.

In Step B, (R,S)-2-(3-oxo-cyclopentyl)-isoindole-1,3-dione (1) is reacted with 4-bromophenylhydrazine hydrochloride in a typical Fischer indole synthesis. Preferred conditions use glacial acetic acid at about 50 to 80° C. for 2 to 24 h.

In Scheme 1, Step C, the phthalimide group of the tetrahydrocyclopenta[b]indole of formula (2) is cleaved with hydrazine or hydrazine hydrate to provide an aminotetrahydrocyclopenta[b]indole of formula (3). Preferred conditions use tetrahydrofuran/ethanol in a mixture of about 20/1 by volume at a temperature of about 40 to 70° C., for 1 to 12 hours. The resulting phthalhydrazide is removed by filtration and the product isolated by concentration of the filtrate.

In Step D, the amine of formula (3) is protected with a t-boc group to give the protected amine of formula (4). Preferred conditions use di-tert-butyldicarbonate in an inert solvent such as THF or dioxane, in the presence of an inorganic base such $NaHCO_3$. In Step E, the racemic t-boc material of formula (4) is resolved using chiral HPLC to obtain the (S) enantiomer of formula (5).

In Step F, the (S) bromo carbamate of formula (5) is converted to the nitrile of formula (6). The reaction is run in an inert solvent, such as N,N'-dimethylacetamide in the presence of a mixture of zinc acetate or zinc formate, zinc cyanide, and zinc dust. A palladium catalyst is used, such as [1,1'-bis(diphenylphosphino)ferrocene]dichloro palladium(II) or as a complex with dichloromethane. Alternatively, the catalyst may be formed in situ using palladium metal and the appropriate ligand. The reaction is heated at about 80 to 120° C. for about 2 to 24 h.

In Step G, the boc group is removed using typical acidic conditions such as HCl/dioxane or TFA to obtain the chiral amine, which is then acylated with isopropyl chloroformate to give a carbamate of formula (7), using conditions well known to those skilled in the art. The amine is combined with an excess of an organic amine base such as triethylamine or diisopropylethylamine in an inert solvent such as tetrahydrofuran, toluene, dichloroethane or dichloromethane, N-methylpyrrolidinone, or N,N-dimethylformamide, or a mixture thereof. Preferred conditions use diisopropylethylamine in dichloromethane in the presence of isopropylchloroformate at a temperature of about 0 to 40° C. for about 1 to 72 hours. The product is isolated by addition of water and collection of the resulting solid.

In Scheme 2 is depicted an alternate route for the synthesis of an intermediate of formula (7).

In Scheme 2, Step A, the phthalimide group of the tetrahydrocyclopenta[b]indole of formula (2) is cleaved with methylamine to provide an aminotetrahydrocyclopenta[b]indole of formula (3). Preferred conditions use a solvent such as ethanol at a temperature of about 0 to 35° C., for 3 to 24 hours. The resulting by-product is removed by making the pH alkaline and filtering the resultant precipitate. The product is isolated from the filtrate by precipitation with water and 10% NaOH.

In Step B, the racemic aminotetrahydrocyclopenta[b]indole of formula (3) is resolved using (R)-2-hydroxy-3-phenylpropionic acid to obtain the salt of the (S)-aminotetrahydrocyclopenta[b]indole of formula (8). The salt formation is preferably done in isopropanol, with heating for about 1 to 6 hours, followed by cooling to obtain the desired enantiomer.

In Step C, the salt of formula (8) is neutralized to the free base and then acylated to obtain a carbamate of formula (9). The salt is neutralized with about 2 to 3 eq of an organic base such as triethylamine or diisopropylethyl amine in an inert solvent such as toluene, followed by acylation with isopropylchloroformate.

In Scheme 2, Step D, the bromo carbamate of formula (9) is converted to the nitrile of formula (7) as previously described for Scheme 1, Step F.

Preparation 1

(R,S)-2-(3-Oxo-cyclopentyl)-isoindole-1,3-dione

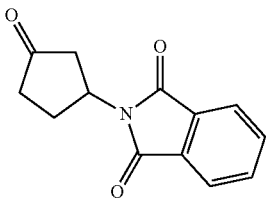

While stirring vigorously with a mechanical stirrer, 2 M aqueous $Na_2CO_3$ (79 mL, 0.158 mol) is added to a slurry of cyclopentenone (100 g, 1.22 mol) and phthalimide (180 g, 1.22 mol) in MeOH (886 mL). After approximately 2 h, a thick white precipitate will form. The mixture is stirred at room temperature for 24 h. The white solid is collected by vacuum filtration and rinsed with methanol (1 L). The solid is suspended in water (1 L) and stirred for 3 h. The solid is collected and dried in a vacuum oven at 40° C. overnight to give 198 g (71%) of the title compound as a white solid. 1H NMR (DMSO-d6) δ 7.85-7.77 (m, 4H), 4.90 (m, 1H), 2.67 (ddd, 1H, J=18.5, 6.2, 1.3 Hz), 2.54 (dd, 1H, J=18.5, 9.2 Hz), 2.45 (m, 1H), 2.32-2.21 (m, 3H); ES/MS m/z 230 (M+1, weak). NOTE: The product will readily undergo the retro-Michael reaction upon treatment with aqueous base.

Preparation 2

(R,S)-2-(7-Bromo-1,2,3,4-tetrahydro-cyclopenta[b]indol-2-yl)-isoindole-1,3-dione

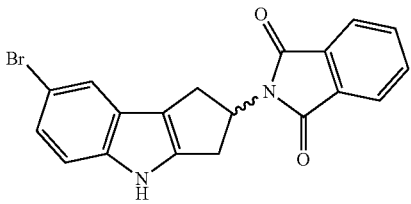

In a 5 L flask is mixed (R,S)-2-(3-oxo-cyclopentyl)-isoindole-1,3-dione (295.3 g, 1.29 mol), 4-bromophenyl hydrazine-HCl (287.9 g, 1.29 mol) and glacial acetic acid (3 L) with mechanical stirring. The reaction is refluxed for 5 h, and then cooled to room temperature. The reaction is poured into water (4 L) with rapid stirring. The solid is collected by vacuum filtration, washed with water (4 L), and air-dried for 30 min. The solid is slurried with MeOH (700 mL), collected by vacuum filtration and rinsed with MeOH (100 mL). The gray solid is air dried for 2 h, then dried overnight in a 50° C. vacuum oven to obtain 414.67 g (84%) of the title compound as a dark solid. ES/MS m/z ($^{79}$Br/$^{81}$Br) 381/383 [M+H]$^+$.

Preparation 3

(R,S)-7-Bromo-1,2,3,4-tetrahydro-cyclopenta[b]indol-2-ylamine

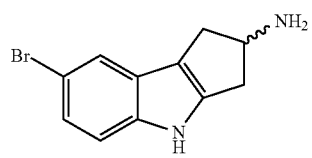

To a solution of (R,S)-2-(7-bromo-1,2,3,4-tetrahydro-cyclopenta[b]indol-2-yl)-isoindole-1,3-dione (150 g, 393 mmol) in THF (1000 mL) and EtOH (150 mL) is added hydrazine monohydrate (35.0 g, 34.0 mL, 699 mmol). The reaction mixture is stirred with mechanical stirring at room temperature for 18 h and then for 2 h at 55° C., whereupon the reaction becomes very viscous and THF (425 mL) and EtOH (75 mL) are added. Heating at 55° C. is continued for another 2 h. The reaction is cooled to room temperature, filtered through diatomaceous earth, rinsed with THF, and concentrated to dryness. The residue is mixed with toluene and EtOH and concentrated again to dryness. The product is placed under high vacuum for 3 h, yielding 94 g (95%) of the title compound as a solid. LC-ES/MS m/z ($^{79}$Br/$^{81}$Br) 251/253 [M+H]$^+$, $T_R$=1.14 min.

Preparation 4

((R,S)-7-Bromo-1,2,3,4-tetrahydro-cyclopenta[b]indol-2-yl)-carbamic acid tert-butyl ester

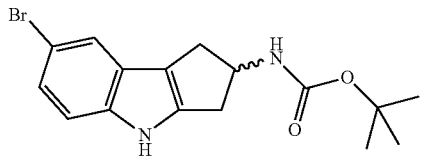

A mixture of (R,S)-7-bromo-1,2,3,4-tetrahydro-cyclopenta[b]indol-2-ylamine (81.5 g, 325 mmol) in THF (800 mL) and saturated aqueous $NaHCO_3$ (200 mL) is treated with di-tert-butyldicarbonate (80.3 g, 357 mmol) portionwise and stirred at room temperature for one hour. The reaction is diluted with EtOAc (300 mL) and brine (100 mL). The layers are separated and the organic layer is dried over $MgSO_4$, filtered, and concentrated to a dark oily solid. The solid is mixed with $CH_2Cl_2$ (400 mL), cooled in an ice bath, and filtered. The solid is rinsed with $CH_2Cl_2$ and hexanes to recover 28.1 g (34%) of the title compound as a solid. An additional 78.8 g (60%) of the title compound is obtained by concentrating the filtrate and purifying by chromatography (1 L silica gel, loaded as a concentrated $CH_2Cl_2$ solution and eluted with 30% hexanes/$CH_2Cl_2$, 100% $CH_2Cl_2$, then 3% EtOAc/$CH_2Cl_2$). $^1$H-NMR (400 MHz, CDCl$_3$) δ 7.98-7.91 (m, 1H), 7.54 (s, 1H), 7.25 (s, 2H), 7.20-7.15 (m, 2H), 5.05-5.02 (m, 2H), 3.37-3.29 (m, 2H), 2.77-2.70 (m, 1H), 2.62-2.57 (m, 1H), 1.46 (s, 9H).

Preparation 5

((S)-7-Bromo-1,2,3,4-tetrahydro-cyclopenta[b]indol-2-yl)-carbamic acid tert-butyl ester

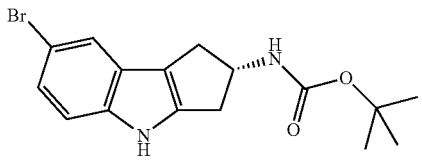

((R,S)-7-Bromo-1,2,3,4-tetrahydro-cyclopenta[b]indol-2-yl)-carbamic acid tert-butyl ester (635 g, 1810 mmol) is first triturated with cold Et$_2$O and then purified by chiral HPLC (column: Chiralcel OJ 8×32 cm; eluent: 100% MeOH) to afford 310 g of the title compound (second-eluting isomer) as a tan solid. Chiral HPLC OJ-H, 100% MeOH, UV detection@250 nm $T_R$=7.6 min, 97.8% ee.

Preparation 6

((S)-7-Cyano-1,2,3,4-tetrahydro-cyclopenta[b]indol-2-yl)-carbamic acid tert-butyl ester

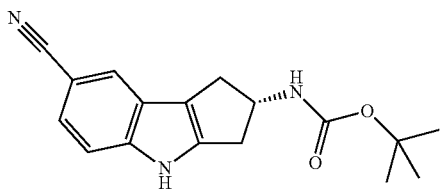

The following reagents are stirred together in DMF (250 mL) at 100° C. for 18 h: ((S)-7-bromo-1,2,3,4-tetrahydro-cyclopenta[b]indol-2-yl)-carbamic acid tert-butyl ester (50.0 g, 142 mmol), zinc cyanide (11.9 g, 99.7 mmol), zinc acetate (5.22 g, 28.5 mmol), 1,1'-bis(diphenylphosphino)ferrocene) palladium (II) chloride (Pd(dppf)$_2$Cl$_2$) (1.74 g, 2.14 mmol), and zinc (3.72 g, 56.9 mmol). The reaction is concentrated to dryness and partitioned between water and ethyl acetate. The organics are washed with water and brine, then concentrated to afford a solid. The solid is chromatographed in two equal portions on silica gel (1600 mL) as follows: load as a solution in CH$_2$Cl$_2$ and elute with 2% EtOAc in CH$_2$Cl$_2$ (3 L), then 5% EtOAc in CH$_2$Cl$_2$. The product is recovered from the two columns to give 29 g (69%) of the title compound as a white solid. $^1$H-NMR (400 MHz, CDCl$_3$) δ 8.39 (s, 1H), 7.74 (s, 1H), 7.34 (d, J=1.8 Hz, 2H), 5.05-4.96 (m, 2H), 3.37-3.25 (m, 2H), 2.80-2.63 (m, 2H), 1.46 (s, 9H).

Preparation 7

((S)-7-Cyano-1,2,3,4-tetrahydro-cyclopenta[b]indol-2-yl)-carbamic acid isopropyl ester

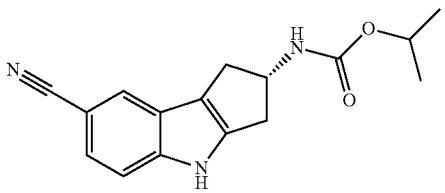

((S)-7-Cyano-1,2,3,4-tetrahydro-cyclopenta[b]indol-2-yl)-carbamic acid tert-butyl ester (10 g, 33.63 mmol) is dissolved in 1,4-dioxane (102 mL) and treated with 4 M HCl/dioxane (102 mL) at room temperature. After 18 h a solid is filtered off and washed with Et$_2$O (50 mL) and then dried in vacuo.

The solid is slurried in dichloromethane (168 mL) and treated with diisopropylethylamine (12.3 mL, 70.1 mmol) and isopropyl chloroformate (1.0 M in toluene, 34.0 mL, 34.0 mmol) at room temperature. After 4 h the reaction is treated with water (50 mL) and concentrated to give an aqueous slurry of the product. The reaction is further diluted with water (500 mL) and sonicated for 15 min in an ultrasonic bath. A tan solid is filtered off and dried in vacuo at 40° C. The solid is slurried in Et$_2$O (100 mL), sonicated for 10 min in an ultrasonic bath, filtered, washed with Et$_2$O (50 mL), and then dried in vacuo to give 8.20 g (86%) of the title compound as a tan solid. LC-ES/MS m/z 284 [M+H]$^+$, 282 [M−H]$^-$, $T_R$=2.20 min; $^1$H-NMR (400 MHz, DMSO-d$_6$) δ 11.44 (s, 1H), 7.78 (s, 1H), 7.52 (d, J=7.5 Hz, 1H), 7.39 (d, J=8.4 Hz, 1H), 7.28 (dd, J=1.8, 8.4 Hz, 1H), 4.77-4.63 (m, 2H), 3.18-3.04 (m, 2H), 2.70 (dd, J=6.2, 15.8 Hz, 1H), 2.58 (dd, J=6.2, 14.5 Hz, 1H), 1.13 (d, J=6.2 Hz, 6H).

Alternative synthesis of ((S)-7-Cyano-1,2,3,4-tetrahydro-cyclopenta[b]indol-2-yl)-carbamic acid isopropyl ester Preparation 8

(R,S)-7-Bromo-1,2,3,4-tetrahydro-cyclopenta[b]indol-2-ylamine

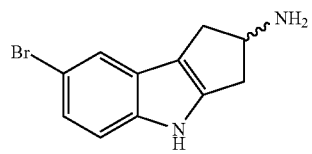

To a 3-neck round bottom flask is added (R,S)-2-(7-bromo-1,2,3,4-tetrahydrocyclopenta[b]indol-2-yl)-isoindole-1,3-dione (170.00 g, 445.93 mmol) and methylamine in EtOH (510 mL, 510.00 mmol) at 25° C. under nitrogen. The mixture is held at 20-25° C. with stirring for 14 h. The starting materials are dissolved to form a brown solution with some observable brown precipitate. The reaction mixture is monitored by HPLC which shows that less than 2% of starting material is remaining. The mixture is stirred for one hour and the pH is adjusted to 11 with NaOH solution. The mixture is filtered and the solid (by-product) is washed with EtOH (170 mL). To the filtrate is added water (3400 mL) and 10% NaOH solution (600 mL) over 30 min at room temperature. The pH becomes 12 and a brown solid precipitates. The solid is filtered and the cake is dried at 60° C. under vacuum to provide 103 g (89%) of a light brown solid.

Preparation 9

(S)-7-Bromo-1,2,3,4-tetrahydro-cyclopenta[b]indol-2-ylamine(R)-2-hydroxy-3-phenylpropionic acid salt

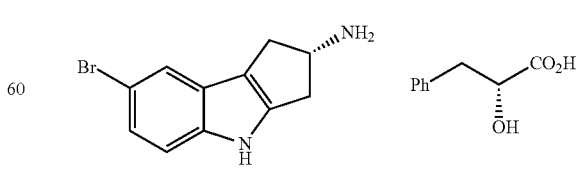

To a 3-neck round bottom flask is added is added (R,S)-7-bromo-1,2,3,4-tetrahydro-cyclopenta[b]indol-2-ylamine (94.00 g, 361.66 mmol) and (R)-2-hydroxy-3-phenylpropionic acid (36.00 g, 0.60 eq, 216.64 mmol). Then IPA (180 mL) and EtOH (180 mL) are added slowly to the mixture at 25° C. A slurry is observed. The slurry is held at 80° C. with stirring for 2 h. A brown cloudy solution is formed. The mixture is cooled to 60° C. for one hour, and then stirred at 25° C. for 2 h. The mixture is then stirred at −10° C. for one hour. The solid is filtered and the cake is washed with IPA (10 mL) and n-heptane (10 mL). The wet solid is dried at 60° C. under vacuum for 4 h to yield 66.1 g (43.5%) of a light yellow solid. HPLC/MS: 99.3% purity. Chiral HPLC: % (Chiralcel OJ-RH, 100% MeOH with 0.2% diethylmethylamine, UV detection@230 nm, 99.62% ee.

Preparation 10

((S)-7-Bromo-1,2,3,4-tetrahydro-cyclopenta[b]indol-2-yl)-carbamic acid isopropyl ester

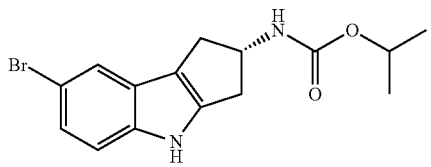

(S)-7-Bromo-1,2,3,4-tetrahydro-cyclopenta[b]indol-2-ylamine(R)-2-hydroxy-3-phenylpropionic acid salt (60.00 g, 143.78 mmol) and diisopropylethylamine (50 mL, 296.12 mmol) are combined in toluene (165 mL). The reaction vessel is purged with nitrogen three times. The mixture is cooled to 0° C. with stirring and is held at that temperature for 30 min. A solution of isopropyl chloroformate (20.00 g, 163.20 mmol) in toluene (165 mL) is added at 0-5° C. over 10 min. The mixture is stirred at 5° C. for 10 min. HPLC shows 98.6% complete. The reaction is quenched with water (1 L) and ethyl acetate (480 mL). The mixture is filtered and the solid is washed with ethyl acetate (2×240 mL). The combined organic layer is washed with brine twice, dried (MgSO$_4$), and filtered. The organic solvent is reduced to 50 mL. The mixture is cooled to 25° C. and tert-butyl methyl ether (50 mL) and ethyl acetate (50 mL) are added. An off-white solid is precipitated. The solid is filtered and washed with heptanes (100 mL). The solid is dried under vacuum at 50° C. for 4 h to give 44.4 g (90.3%) of a light brown solid.

Preparation 11

((S)-7-Cyano-1,2,3,4-tetrahydro-cyclopenta[b]indol-2-yl)-carbamic acid isopropyl ester

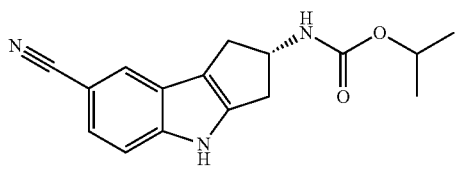

A 50 L round bottom flask is charged with dimethylacetamide (33 L, 10 volumes) and a sub-surface nitrogen sparge is initiated for 30 min. The flask is then charged with zinc acetate (363 g, 1.98 mol) in one portion. Then Pd(dppf)$_2$Cl$_2$, complex with dichloromethane (1:1) (266 g, 0.327 mol, 3.3 mol %) is added in one portion followed by the addition of zinc cyanide (697 g, 5.93 mol, 0.6 eq.) in one portion. ((S)-7-Bromo-1,2,3,4-tetrahydro-cyclopenta[b]indol-2-yl)-carbamic acid isopropyl ester (3335 g, 9.89 mol) is added in one portion and the mixture is sparged with sub-surface nitrogen for 20 min. Finally, zinc dust (259 g, 3.96 mol) is added in one portion and the reaction is heated to 100° C. to 110° C. for 6 h. The reaction is deemed complete when there is <1% starting material by HPLC. After the reaction is complete, the heat is turned off and the reaction is cooled to room temperature. The reaction is then filtered and rinsed with dimethyl acetamide (3×3 L). The filtrate is then poured over water (60 L) and the resulting slurry is stirred for a minimum of 2 h. The slurry is then filtered and rinsed with water (20 L). The wet cake is then dissolved in tert-butyl methyl ether/acetone (1:1, 60 L total) and stirred for a minimum of 30 min. The mixture is then filtered to remove inorganic salt. The filtrate is charged back to the tank. The organic layer is washed with an aqueous solution of 10% 2,4,6-trimercapto-s-triazine (TMT) (2×20 L). The organic layer is then charged with charcoal (330 g, 10% wt), Florisil® (330 g, 10% wt), and magnesium sulfate to dry the layer. The mixture is stirred at room temperature for a minimum of 2 h. The mixture is then filtered and rinsed with acetone. The filtrate is then concentrated under pressure and co-evaporated with heptane. The resulting slurry is then filtered and rinsed with heptane. The solids are collected and dried to a constant weight (2520 g, 90%). LC-ES/MS m/z 284 [M+H]$^+$, 282 [M−H]$^-$.

Alternate Cyanation Method:

((S)-7-Bromo-1,2,3,4-tetrahydro-cyclopenta[b]indol-2-yl)-carbamic acid isopropyl ester (50 g, 148.27 mmol), zinc cyanide (10.45 g, 88.99 mmoles), and palladium (6.31 g, 2.96 mmol) are combined in dimethylacetamide (500 mL). The resulting slurry is sparged with sub-surface nitrogen for 10 min. Then 1,1'-bis(diphenylphosphino)ferrocene (3.29 g, 5.93 mmol) is added and the reaction is sparged for another 10 min. Finally, zinc formate (2.3 g, 14.80 mmol) is added and the reaction is sparged again for 10 min. The reaction is then placed under a nitrogen sweep and heated up to 110° C. overnight. The heat is turned off. The reaction is cooled to 85° C. and 3-mercaptopropyl-functionalized silica gel (5 g, 10 wt %) is added. The mixture is stirred for 2 h while cooling to room temperature. The reaction mixture is then filtered and the solid is rinsed with DMAC (50 mL). To the stirring orange filtrate is added 0.3 M ethylenediaminetetraacetic acid tetrasodium salt in water (1000 mL) over 10 min. The resulting slurry is stirred at room temperature and is filtered. The solid is rinsed with 0.3 M ethylenediaminetetraacetic acid tetrasodium salt (250 mL) followed by water (250 mL). A light brown solid is collected and dried overnight in the vacuum oven to provide the product (42.44 g) in quantitative yield.

Preparation 12

[(2R,3S)-3-hydroxytetrahydrofuran-2-yl]methyl 4-methylbenzenesulfonate

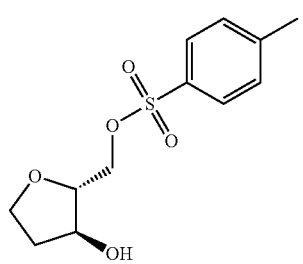

(2R,3S)-2-(hydroxymethyl)tetrahydrofuran-3-ol (1.59 g, 13.46 mmol) (prepared as described in Chenault, K. H.; Mandes, R. F. Tetrahedron, 1997, 53(32), 11033-11038) is dissolved in dry pyridine (15 mL) and the solution cooled to −40° C. in a dry ice/acetone bath for 30 min. p-Toluenesulfonyl chloride (2.58 g, 13.51 mmol) is added slowly over 5 min and the solution allowed to warm up to room temperature over 4 h. The solution is concentrated to provide 3.59 g (86%) of the title compound which is used without further purification.

LC-ES/MS m/z 295.0 [M+Na]⁺, $T_R$=1.76 min. (Symyx Draw 3.1 (IUPAC Name) provides the name for the compound of Preparation 12.)

Example 1

[(S)-7-Cyano-4-((2R,3S)-3-hydroxytetrahydrofuran-2-ylmethyl)-1,2,3,4-tetrahydrocyclopenta[b]indol-2-yl]-carbamic acid isopropyl ester

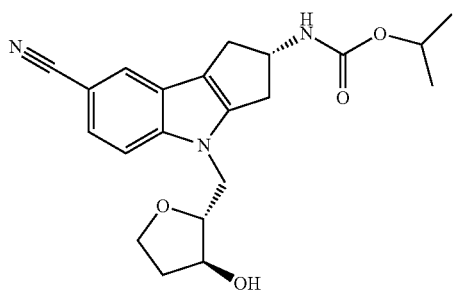

A mixture of ((S)-7-cyano-1,2,3,4-tetrahydro-cyclopenta[b]indol-2-yl)-carbamic acid isopropyl ester (2.50 g, 8.82 mmol), [(2R,3S)-3-hydroxytetrahydrofuran-2-yl]methyl 4-methylbenzenesulfonate (3.10 g, 11.38 mmol), and cesium carbonate (5.00 g, 15.35 mmol) in N-methylpyrrolidine (25 mL) is heated in a 65° C. oil bath overnight. After cooling to ambient temperature, the reaction is diluted with ethyl acetate (120 mL) and washed with water (3×100 mL) and brine. The organic portion is dried over sodium sulfate, filtered, and concentrated to dryness. The resulting residue is purified by medium pressure liquid chromatography, eluting with ethyl acetate. Fractions containing pure product are combined and concentrated to afford 2.46 g (72%) of the title compound. LC-ES/MS m/z 384.2 [M+H]⁺, $T_R$=1.90 min. (Symyx Draw 3.1 (IUPAC Name) provides the following name for the compound of Example 1: Isopropyl N-[(2S)-7-cyano-4-[[(2R,3S)-3-hydroxytetrahydrofuran-2-yl]methyl]-2,3-dihydro-1H-cyclopenta[b]indol-2-yl]carbamate.)

What is claimed is:

1. A compound which is [(S)-7-Cyano-4-((2R,3S)-3-hydroxytetrahydrofuran-2-ylmethyl)-1,2,3,4-tetrahydro-cyclopenta[b]indol-2-yl]-carbamic acid isopropyl ester.

2. A method of treating or preventing hypogonadism, osteoporosis, osteopenia, sarcopenia, cachexia, muscle atrophy, sexual dysfunction or erectile dysfunction comprising administering to a patient in need thereof an effective amount of a compound which is [(S)-7-Cyano-4-((2R,3S)-3-hydroxytetrahydrofuran-2-ylmethyl)-1,2,3,4-tetrahydro-cyclopenta[b]indol-2-yl]-carbamic acid isopropyl ester.

3. The method according to claim 2 for treating or preventing muscle atrophy associated with disuse, trauma, immobilization, spinal cord injury or stroke.

4. The method according to claim 3 for treating or preventing muscle atrophy associated with hip or knee replacement, hip fracture, spinal cord injury or stroke.

5. The method according to claim 4 for treating or preventing muscle atrophy associated with hip or knee replacement or hip fracture.

6. The method according to claim 4 for treating or preventing muscle atrophy associated with spinal cord injury or stroke.

7. A pharmaceutical composition comprising [(S)-7-Cyano-4-((2R,3S)-3-hydroxytetrahydrofuran-2-ylmethyl)-1,2,3,4-tetrahydro-cyclopenta[b]indol-2-yl]-carbamic acid isopropyl ester in combination with one or more pharmaceutically acceptable carriers, excipients, or diluents.

8. The pharmaceutical composition according to claim 7 for the treatment or prevention of hypogonadism, osteoporosis, osteopenia, sarcopenia, cachexia, muscle atrophy, sexual dysfunction or erectile dysfunction.

* * * * *